United States Patent [19]

D'Amico et al.

[11] 4,154,600

[45] May 15, 1979

[54] THIOLCARBAMATES AS PLANT GROWTH REGULATORS

[75] Inventors: John J. D'Amico; Frederic G. Bollinger, both of St. Louis, Mo.

[73] Assignee: Monsanto Company, St. Louis, Mo.

[21] Appl. No.: 532,272

[22] Filed: Dec. 12, 1974

[51] Int. Cl.² ............................................. A01N 5/00
[52] U.S. Cl. ........................................ 71/100; 71/76
[58] Field of Search ................................... 71/76, 100

[56] References Cited

U.S. PATENT DOCUMENTS 3,175,897  3/1965  Tilles et al. ............................ 71/100

Primary Examiner—Catherine L. Mills
Attorney, Agent, or Firm—Arnold H. Cole; Donald W. Peterson

[57] ABSTRACT

The natural growth and development of dicotyledonous crop plants is regulated by treatment with certain ethyl N-alkyl-N-substituted cyclohexane thiolcarbamates.

13 Claims, No Drawings

THIOLCARBAMATES AS PLANT GROWTH REGULATORS

This invention relates to a method of regulating the natural growth and development of desired plants by means of a chemical treatment. More particularly, this invention is concerned with a method whereby the natural growth and development of dicotyledonous crop plants is regulated by applying to such plants certain ethyl N-alkyl-N-substituted cyclohexane thiolcarbamates. As employed herein, the term "natural growth and development" designates the normal life cycle of the plant in accordance with its genetics and its environment, in the absence of artificial, external influences.

It should be understood that the regulation of natural growth and development contemplated herein does not include killing or herbicidal action. Although phytotoxic or lethal amounts of the active ingredients discussed below might be employed to obtain a total inhibition of the treated plants, the present invention involves only the employment of such amounts as will serve to regulate said natural growth and development. As may be expected, and as long understood by those skilled in the art, such effective plant regulating amounts will vary, not only with the particular material used in the treatment, but also with the regulatory effect desired, the species of plant being treated and its stage of development, and whether a permanent or transient regulatory effect is sought. Other factors which may also bear upon the determination of an effective plant regulating amount include the plant growth medium, the manner and situs of application, weather conditions such as temperature and rainfall, and the like.

In accordance with this invention, it has been found the desirable regulation of said natural plant growth and development is achieved by application of a selected active ingredient to seeds, seedlings before or after emergence, roots, stems, leaves, flowers, fruit or other plant parts. Such application can be made directly to one or more of said plant parts, or application may be made indirectly as by treatment of the plant growth medium.

The use of numerous aliphatic esters of carbamic, thiol-, thiono- and dithiocarbamic acids to kill or prevent the growth of undesired plants is well known in the art. The particular use of phytotoxic amounts of alkyl esters of N-alkyl-N-cyclohexylthiolcarbamate is described in U.S. Pat. No. 3,175,897 and U.S. Pat. No. 3,185,720. Unsaturated aliphatic esters of the acids are disclosed for the same purposes in U.S. Pat. No. 3,330,643, and, in addition, this latter patent teaches that the N-cyclohexyl group may contain a methyl substituent thereon. A wide variety of different esters of N-cyclohexylthiolcarbamate is similarly taught in U.S. Pat. No. 3,134,666, U.S. Pat. No. 3,126,406, U.S. Pat. No. 3,055,751 and U.S. Pat. No. 2,989,393. The common feature in each of these patents is the disclosure that the carbamates are employed in the treatment of undesired plants (weeds), and that such treatment serves to kill the existing plants and/or prevent the germination and growth of any new plants.

In accordance with the present invention, it has been found that certain thiolcarbamates of this class can be applied to desirable dicotyledonous crop plants and serve to regulate the natural growth and development of the treated plants. The particular esters which can be employed in the practice of this invention are illustrated by the formula

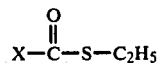

wherein X represents a cyclohexylamino group selected from

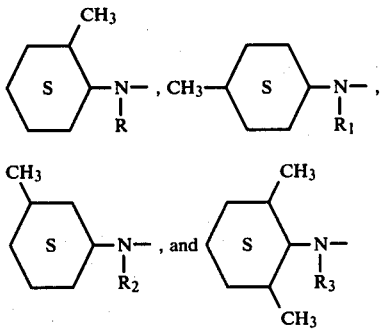

wherein R is methyl, ethyl, n-propyl or n-butyl, $R_1$ is ethyl or n-propyl, $R_2$ is methyl, ethyl, n-propyl, i-propyl or n-butyl, and $R_3$ is ethyl, n-propyl or n-butyl. These compounds can be readily prepared by the methods described in the above-cited patents.

Regulations of the natural growth or development of plants by chemical treatment may result from the effect of the chemical substance on the physiological processes of the plants, or it may be due to the effect of such substance on the morphology of the plant. As should be readily apparent, said regulation may also result from a combined or sequential effect of the chemical in the areas of both physiology and morphology.

In general, regulation of the natural growth or development which leads to a morphological change in the plant is readily noticeable by visual observation. Such changes can be found in the size, shape, color or texture of the treated plant or any of its parts. Similarly, changes in the quantity of plant fruit or flowers can be simply noted.

On the other hand, regulation which leads to changes in the physiological processes occur within the treated plant and are usually hidden from the eye of an observer. Changes of this type are most often in the production, location, storage or use of naturally occurring chemicals, including hormones, within the plant. Physiological changes in a plant may be recognized when followed by a subsequent change in morphology. Additionally, there are numerous analytical procedures known to those skilled in the art for determining the nature and magnitude of changes in the various physiological processes.

The individual compounds of the instant invention serve to regulate the natural growth or development of treated plants in a number of diverse ways, and it is to be understood that each compound may not produce identical regulatory effects on each plant species or at every rate of application. As stated above, responses will vary in accordance with the compounds, the rate, the plant, etc.

Among the particular regulatory responses demonstrated by compounds of this invention can be generally termed retardation of vegetative growth, and such a response has a wide variety of beneficial features. In certain plants this retardation causes a diminution or elimination of the normal apical dominance leading to a shorter main stem and increased lateral branching. This alteration of the natural growth or development produces smaller, bushier plants which often demonstrate increased resistance to drought and pest infestation.

As illustrated in the examples which are hereinafter presented, the individual compounds of the invention regulate the natural growth or development of treated plants in numerous other and different respects. Included among these other regulatory effects are the instigation of axillary bud development, the alteration of leaf shape, the delay or acceleration of setting of fruit or pods, etc. Although regulatory effects such as those described above can be per se desirable, it is most often the ultimate result of these effects upon the economic factor which is of primary significance. Thus, it must be recognized that increases in the yield of individual plants, increases in the yield per unit area, and reductions in the cost of harvesting and/or subsequent processing are all to be considered in any assessment of the consequence of an individual regulatory effect during the growth or development of a plant.

The specific examples which follow are presented as merely illustrative, non-limiting demonstrations of the useful and unexpected regulating properties of various compounds of this invention.

EXAMPLE I

The regulatory effects of compounds of this invention were demonstrated in a series of tests on representative dicotyledonous crop plants. In each of these tests the compounds were formulated in acetone and/or water plus a small amount of a surface active agent, and the specific application rates were varied depending upon the particular compound and the particular test. The particular dicotyledonous crop plants selected for these tests were soybeans, a representative legume, of the Wayne or Corsoy varieties. Untreated control plants were employed for comparison purposes in all tests. The procedures used were as follows:

TEST A

A number of soybean plants are grown from seeds in an aluminum pan for a period of one week. The plants are then thinned to three uniform plants per pan, and the height of each plant is measured to the top of the terminal bud. A solution of the compound being tested is sprayed over the plants in a pan at a selected application rate. All pans are transferred to a greenhouse and watered from below in a sand bench. Each pan is fertilized with 40 ml. of a 1.5% solution of Rapid-Gro about 2 days after treatment. Two weeks after said treatment the height of each plant in the pans is again measured to the top of the terminal bud, other visible effects are noted, and direct comparisons are made with the untreated control plants. In this test, retardation of vegetative growth (stature reduction) is specifically recognized where at least two-thirds of the treated plants show at least 26% less growth than the untreated control plants.

TEST B

A number of soybean plants are grown from seeds in plastic pots, and these are thinned to a single plant per pot just prior to treatment. A solution of the compound being tested is sprayed on plants in several pots, such plants including some that are four weeks old (3-4 trifoliate stage) and some that are 6 weeks old (5-6 trifoliate stage). The treated plants and those in the untreated controls are of approximately the same size at the time of application, and thereafter, all plants are transferred to a greenhouse, and watered and fertilized substantially as set forth above. Two weeks after application the height of each soybean plant is measured to the tip of the terminal bud, other visible effects are noted, and direct comparisons are made with the untreated control plants. Except where specifically noted, the results of tests on the two trifoliate stages are combined and averaged. In this test, retardation of vegetative growth (stature reduction) is specifically recognized where the average height increase of the treated plants is at least 15% less than that of the untreated control plants.

In connection with specific application rates used in Tests A and B in terms of kg./hectare, it should be pointed out that such tests involve treatment of a relatively small number of plants in a pan or pot. Thus, the actual rate of application of the chemical to the plants themselves may be generally somewhat lower than the stated kg./hectare.

The specific compounds employed in the above tests were:

No. 1 Ethyl N-ethyl-N-(2-methylcyclohexyl)thiolcarbamate

No. 2 Ethyl N-ethyl-N-(3-methylcyclohexyl)thiolcarbamate

No. 3 Ethyl N-n-propyl-N-(3-methylcyclohexyl)thiolcarbamate

No. 4 Ethyl N-n-butyl-N-(3-methylcyclohexyl)thiolcarbamate

No. 5 Ethyl N-methyl-N-(2-methylcyclohexyl)thiolcarbamate

No. 6 Ethyl N-n-butyl-N-(2-methylcyclohexyl)thiolcarbamate

No. 7 Ethyl N-ethyl-N-(4-methylcyclohexyl)thiolcarbamate

No. 8 Ethyl N-n-propyl-N-(4-methylcyclohexyl)thiolcarbamate

No. 9 Ethyl N-i-propyl-N-(3-methylcyclohexyl)thiolcarbamate

No. 10 Ethyl N-n-propyl-N-(2,6-dimethylcyclohexyl)thiolcarbamate

No. 11 Ethyl N-n-butyl-N-(2,6-dimethylcyclohexyl)thiolcarbamate

No. 12 Ethyl N-methyl-N-(3-methylcyclohexyl)thiolcarbamate

No. 13 Ethyl N-ethyl-N-(2,6-dimethylcyclohexyl)thiolcarbamate

| Cpd. No. | Test | Kg./Hectare | Regulatory Responses |
|---|---|---|---|
| 1 | A | 5.6 | stature reduction, severe leaf burn |
| 1 | A | 3.36 | stature reduction, leaf distortion, axillary bud development, inhibition of apical development, slight leaf burn |
| 1 | A | (1.34) (.67) | stature reduction, leaf distortion, axillary bud development, inhibition of apical development |
| 1 | B | 5.6 | stature reduction, leaf distortion, necrosis, leaf |

-continued

RESULTS

| Cpd. No. | Test | Kg./Hectare | Regulatory Responses |
|---|---|---|---|
| 1 | B | 2.8 | alteration, slight leaf burn stature reduction, leaf distortion, leaf alteration, delayed flowering, slight leaf burn |
| 1 | B | 1.4 | stature reduction, leaf distortion, slight leaf burn |
| 2 | A | 6.72 | stature reduction, leaf distortion, slight leaf burn |
| 2 | A | 3.36 | stature reduction, leaf distortion, axillary bud development, inhibition of apical development, slight leaf burn |
| 2 | A | 1.34 | stature reduction, leaf distortion, inhibition of apical development |
| 2 | A | .67 | stature reduction, inhibition of apical development |
| 2 | B(3rd) | 2.8 | stature reduction, leaf distortion, axillary bud development, altered canopy, dark foliar color, inhibition of apical development |
| 2 | B(5th) | 2.8 | stature reduction, leaf distortion, enhanced pod set |
| 3 | A | 6.72 | axillary bud development, leaf distortion, moderate leaf burn |
| 3 | A | 3.36 | stature reduction, axillary bud development, leaf distortion, inhibition of apical development, slight to moderate leaf burn |
| 3 | A | 1.34 | stature reduction, axillary bud development, leaf distortion, inhibition of apical development, slight leaf burn |
| 3 | A | .67 | stature reduction, axillary bud development, leaf distortion, altered canopy, inhibition of apical development, slight to no leaf burn |
| 3 | B(3rd) | 2.8 | stature reduction, axillary bud development, leaf distortion, altered canopy, inhibition of apical development, dark foliar color, slight to no leaf burn |
| 3 | B(5th) | 2.8 | stature reduction, leaf distortion, inhibition of apical development |
| 4 | A | 6.72 | stature reduction, |

-continued

RESULTS

| Cpd. No. | Test | Kg./Hectare | Regulatory Responses |
|---|---|---|---|
| | | | axillary bud development, leaf distortion, slight leaf burn |
| 4 | A | 3.36 | stature reduction, axillary bud development, leaf distortion, inhibition of apical development, slight to no leaf burn |
| | | (1.34) (.67) | stature reduction, axillary bud development, leaf distortion, inhibition of apical development |
| 4 | B(3rd) | 2.8 | stature reduction, axillary bud development, leaf distortion, dark foliar color, inhibition of apical development |
| 4 | B(5th) | 2.8 | stature reduction, leaf distortion, inhibition of apical development, inhibition of axillary buds |
| 5 | A | 6.72 | stature reduction, axillary bud development, leaf distortion, slight leaf burn |
| 5 | A | 3.36 | stature reduction, axillary bud development, leaf distortion, inhibition of apical development |
| 5 | B(3rd) | 2.8 | stature reduction, axillary bud development, leaf distortion, inhibition of apical development, slight leaf burn |
| 5 | B(5th) | 2.8 | leaf distortion |
| 5 | B(5th) | 1.12 | altered canopy |
| 6 | A | 6.72 | axillary bud development, leaf distortion, slight leaf burn |
| 6 | A | (3.36) (1.34) (.67) | stature reduction, axillary bud development, leaf distortion, inhibition of apical development |
| 6 | B(3rd) | 2.8 | stature reduction, axillary bud development, leaf distortion, altered canopy, slight to no leaf burn |
| 6 | B(5th) | 2.8 | stature reduction, leaf distortion |
| 7 | A | 6.72 | stature reduction, axillary bud development, leaf distortion, inhibition of apical development, slight leaf burn |
| 7 | A | (3.36) (1.34) (.67) | stature reduction, axillary bud development, leaf |

RESULTS

| Cpd. No. | Test | Kg./Hectare | Regulatory Responses |
|---|---|---|---|
|  |  |  | distortion, inhibition of apical development |
| 7 | B(3rd) | 2.8 | stature reduction, axillary bud development, leaf distortion, inhibition of apical development, dark foliar color, altered canopy, slight leaf burn |
| 7 | B(5th) | 2.8 | stature reduction, leaf distortion, enhanced pod set, slight leaf burn |
| 7 | B(3rd) | 1.68 | stature reduction, leaf distortion, inhibition of apical development |
| 7 | B(5th) | 1.68 | stature reduction, leaf distortion, delayed and inhibited pod set |
| 8 | A | 6.72 | axillary bud development, leaf distortion |
| 8 | A | (3.36) (1.34) (.67) | axillary bud development, leaf distortion, inhibition of apical development |
| 8 | B(3rd) | 5.6 | stature reduction, axillary bud development, leaf distortion, altered canopy, inhibition of apical development, slight leaf burn |
| 8 | B(5th) | 5.6 | stature reduction, leaf distortion, slight leaf burn |
| 8 | B(3rd) | 2.8 | stature reduction, leaf distortion, inhibition of apical development, slight to no leaf burn |
| 8 | B(5th) | 2.8 | stature reduction, leaf distortion, delayed pod set |
| 9 | A | 3.36 | stature reduction, axillary bud development, leaf distortion, inhibition of apical development, slight to no leaf burn |
| 9 | A | (1.34) (.67) | stature reduction, axillary bud development, leaf distortion, inhibition of apical development |
| 9 | B(3rd) | 2.8 | stature reduction, leaf distortion, altered canopy, inhibition of apical development, inhibition of axillary buds, slight to no leaf burn |
| 9 | B(5th) | 2.8 | stature reduction, leaf distortion |
| 10 | A | 6.72 | stature reduction, axillary bud development, inhibition of apical development, slight leaf burn |
| 10 | A | 3.36 | stature reduction, axillary bud development, leaf distortion, inhibition of apical development |
| 10 | B(3rd) | 2.8 | leaf alteration, leaf inhibition, slight to no leaf burn |
| 10 | B(5th) | 2.8 | enhanced pot set |
| 11 | A | 6.72 | axillary bud development, moderate leaf burn |
| 11 | A | 3.36 | stature reduction, axillary bud development, leaf distortion, inhibition of apical development |
| 11 | B(3rd) | 2.8 | axillary bud development, leaf distortion, slight to no leaf burn |
| 11 | B(5th) | 2.8 | stature reduction |
| 12 | A | 6.72 | stature reduction, leaf distortion, slight leaf burn |
| 13 | A | 3.36 | axillary bud development, leaf distortion, slight leaf burn |

In the results just described, the list of regulatory responses have been combined where the same test was conducted more than once at the same rate. The notation (3rd) or (5th) following the Test B designation indicates the trifoliate stage of the plant at treatment. Where two or more rates are in parentheses together, the regulatory results indicated were the same for each rate.

EXAMPLE II

In this test, soybeans of the Wayne variety were planted in a field in 30.5 and 76.2 cm. rows at a seeding rate of 9 seeds per 30.5 cm. The soil was pre-fertilized, and it was given a treatment with a pre-emergent herbicide spray. The chemicals tested were applied early in the flowering period (about 10% of the total blooms had formed). Five adjacent plants were selected for uniformity in each test, and these were sprayed as a unit with 16.4 ml. of a 50:50 mixture of solvent containing the chemical and water containing 0.05% of Aerosol OT. Each chemical was applied at 3 rates on 2 row spacings using two replications of 5 plants each per treatment. Observations of regulatory responses were made two weeks after treatment, and certain quantitative data were collected at harvest. Untreated control plants were included in the tests and served as the basis for direct comparisons.

Specific application rates employed were equivalent to 1, 2 and 5 mg. per plant, and the compounds applied were No. 2, 3, 4 and 8. The responses noted at the two week observation date were slight leaf burn with all three rates of No. 2, stature reduction and dark foliar color at the highest rate of No. 3, and leaf distortion at the highest rate of No. 8.

At harvest of the soybeans planted in 30.5 cm. rows, it was found that increases occurred in several of the measured factors. With No. 2 at the 2 mg. rate, the number of pods was 107% of control, and the pod weight was 109% of control. With the same chemical at the 1 mg. rate, the number of pods was 108% of control while pod weight was 95% of control. With No. 3 at the 2 mg. rate, the number of pods was 123% of control, pod weight was 136% of control, seed size was 102% of control, and seed yield was 142% of control. With the same chemical at the 1 mg. rate, the number of pods was 106% of control, and the pod weight was 103% of control. With No. 4 at the 5 mg. rate, the number of pods was 100% of control, and the pod weight was 114% of control. With No. 8 at the 2 mg. rate, the number of pods was 126% of control, and pod weight was 130% of control. Yield increases were not observed in the other tests with the compounds of this invention with this row spacing.

At harvest of the soybeans planted in 76.2 cm. rows, it was found that with No. 3 at the 2 mg. rate, the number of pods was 107% of control, pod weight was 105% of control, seed size was 106% of control, and seed yield was 107% of control. With No. 4 at the 5 mg. rate, the number of pods was 117% of control, and pod weight was 104% of control. Yield increases were not observed in the other tests with the compounds of this invention with this row spacing.

EXAMPLE III

In this test, soybeans of the Wayne or cutler variety were planted in three widely spaced field locations in large plots. The plants were sprayed with an emulsifiable concentrate formulation of No. 3, some at the early flowering stage of development and the remainder about 2 weeks later. Applications at each date were at rates of 1.12 and 0.56 kg. per hectare. At harvest, measurements were made of the yield of beans and the size of seeds. The latter measurement was not made for the earlier application at the first location.

At said first location, a yield decrease was noted at the lower application rate on the earlier date, and a yield increase was noted with the same rate at the later application. No yield change was noted in either application at the higher rate. An increase in seed size was noted at both rates of the later application. At the second location, all applications gave an increase in yield. Seed size at said second location increased at the higher rate with the early application and at the lower rate with the later application. There was no change in seed size at the lower rate of early application, and the higher rate of later application gave a decrease in seed size. At the third location, yield increase was noted with the lower rate at both application dates. The higher rate gave no change in yield at early application and a decrease at later application. Seed size showed no change at the higher rate of early application, and all other applications gave an increased seed size.

EXAMPLE IV

In this test, soybeans of the Wayne, Williams and Clark varieties were planted in field plots. The plots were seeded with about 60,700 seeds per hectare with a row width of about 50.1 cm. About 40 days after planting, a formulation of No. 3 with a small amount of surfactant was applied by spraying at rates of 0.56 and 0.28 kg. per hectare. At harvest, measurements were made of yield of beans and seed size.

With regard to seed size, the treated plants were approximately the same as the control at both rates on all three varieties. The Clark variety showed yield increases of 3.0% and 5.1% at the lower and higher rates respectively, while the Wayne variety showed increases of 9.6% and 2.9% at said rates. On the Williams variety, there was no change at the lower rate and a 1.7% decrease at the higher rate. Averaging the yield data on the three varieties gave a 4% increase at the lower rate and a 2% increase at the higher rate.

From the illustrative data presented in foregoing examples of individual compounds of this invention on representative dicotyledonous crop plants, it should be clear that regulatory response will be dependent upon the compound employed, the rate of application, the plant species and its stage of development, and other factors well understood by those skilled in the art.

The plant regulating compositions, including concentrates which require dilution prior to application to the plants, of this invention contain at least one active ingredient and an adjuvant in liquid or solid form. The compositions are prepared by admixing the active ingredient with an adjuvant including diluents, extenders, carriers and conditioning agents to provide compositions in the form of finely-divided particulate solids, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these. From the viewpoint of economy and convenience, water is the preferred diluent.

The plant regulating compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g. sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate and sodium N-methyl-N-(long chain acid) laurates.

Water-dispersible powder compositions can be made containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The water-dispersible powder of this invention usually contains from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total composition. Where required, from about 0.1 to 2.0 parts by weight of the solid inert extender can be replaced by a corrosion inhibitor or anti-foaming agent or both.

Aqueous suspensions can be prepared by mixing together and grinding an aqueous slurry of water-insoluble active ingredient in the presence of dispersing agents to obtain a concentrated slurry of very finely-divided particles. The resulting concentrated aqueous suspension is characterized by its extremely small particle size, so that when diluted and sprayed, coverage is very uniform.

Emulsifiable oils are usually solutions of active ingredient in water-immiscible or partially water-immiscible solvents together with a surface active agent. Suitable solvents for the active ingredient of this invention include hydrocarbons and water-immiscible ethers or ketones. The emulsifiable oil compositions generally contain from about 5 to 95 parts active ingredient, about 1 to 50 parts surface active agent and about 4 to 94 parts solvent, all parts being by weight based on the total weight of emulsifiable oil.

When operating in accordance with the present invention, effective plant regulating amounts of the active ingredients are applied directly or indirectly to the plants. The application of liquid and particulate solid plant regulating compositions can be carried out by conventional methods, e.g. power dusters, boom and hand sprayers and spray dusters. The compositions can also be applied from airplanes as a dust or a spray because of their effectiveness at low dosages.

The application of an effective plant regulating amount of the compounds of this invention to the plant is essential and critical for the practice of the present invention. The exact amount of active ingredient to be employed is dependent upon the response desired in the plant as well as such other factors as the plant species and stage of development thereof, and the environmental conditions, as well as the specific chemical employed. In general, the active ingredients are employed in effective plant regulating amounts equivalent to from about 0.11 to about 11.2 kg. per hectare. It should be understood that the amount of active ingredient employed must be sufficient to regulate the natural growth or development of the treated plants without producing a herbicidal or killing effect on such plants. It is believed that those skilled in the art can readily determine from the teachings of this specification, including examples, the appropriate application rates.

Although the invention is described with respect to specific modifications, the details thereof are not to be construed as limitations except to the extent indicated in the following claims.

What is claimed is:

1. A method of regulating the natural growth and development of dicotyledonous crop plants which comprises applying to said plants an effective plant regulating, non-lethal amount of a compound of the formula

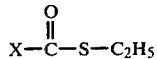

wherein X represents a cyclohexylamino group selected from

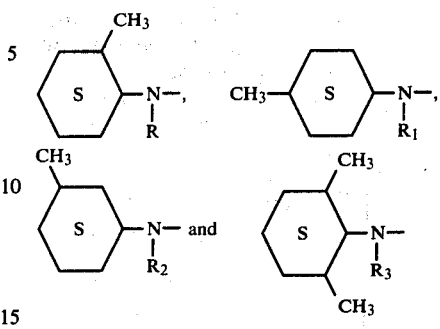

wherein R is methyl, ethyl, n-propyl or n-butyl, $R_1$ is ethyl or n-propyl, $R_2$ is methyl, ethyl, n-propyl, i-propyl or n-butyl, and $R_3$ is ethyl, n-propyl or n-butyl.

2. A method as defined in claim 1 wherein said plants are legume plants.

3. A method as defined in claim 2 wherein said plants are soybean plants.

4. A method as defined in claim 1 wherein X is

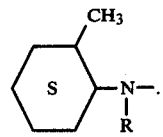

5. A method as defined in claim 1 wherein X is

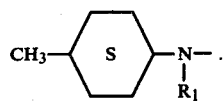

6. A method as defined in claim 1 wherein X is

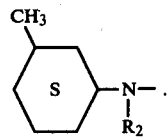

7. A method as defined in claim 1 wherein X is

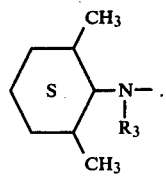

8. A method as defined in claim 6 wherein $R_2$ is n-propyl.

9. A method as defined in claim 6 wherein $R_2$ is n-butyl.

10. A method as defined in claim 6 wherein $R_2$ is ethyl.

11. A method as defined in claim 5 wherein $R_1$ is n-propyl.

12. A method as defined in claim 1 wherein R, $R_1$, $R_2$ and $R_3$ are ethyl.

13. A method as defined in claim 1 wherein R, $R_1$, $R_2$ and $R_3$ are n-propyl.

* * * * *